US00PP30710P3

(12) United States Plant Patent
Wood

(10) Patent No.: US PP30,710 P3
(45) Date of Patent: Jul. 16, 2019

(54) ***DASIPHORA* PLANT NAMED 'SMNPPS'**

(50) Latin Name: *Dasiphora fruiticosa*
Varietal Denomination: SMNPPS

(71) Applicant: Timothy Wood, Spring Lake, MI (US)

(72) Inventor: Timothy Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 15/732,454

(22) Filed: Nov. 14, 2017

(65) Prior Publication Data

US 2019/0150344 P1 May 16, 2019

(51) Int. Cl.
*A01H 5/02* (2018.01)

(52) U.S. Cl.
USPC ..... Plt./237

(58) Field of Classification Search
USPC ..... Plt./237

CPC ..... A01H 5/02; A01H 5/0216; A01H 5/00; A01H 6/74

See application file for complete search history.

(56) References Cited

PUBLICATIONS

Eriksson et al. Phylogenetic analysis of *Potentilla* using DNA sequences of nuclear ribosomal internal transcribed spacers (ITS), and implications for the classification of Rosoideae (Rosaceae), Pl. Syst. Evol. 211: 155-179 (1998). (Year: 1998).*

Oregon State University Landscape Plants *Potentilla fruticosa*, retrieved on Sep. 27, 2018, retrieved from the Internet at https://landscapeplants.oregonstate.edu/plants/potentilla-fruticosa, 2018, pp. 1-3. (Year: 2018).*

* cited by examiner

*Primary Examiner* — June Hwu
(74) *Attorney, Agent, or Firm* — Cassandra Bright

(57) ABSTRACT

A new and distinct *Dasiphora* cultivar named 'SMNPPS' is disclosed, characterized by large, single pink flowers on round, compact plants. The new variety is a *Dasiphora* normally produced as an outdoor garden or container plant.

2 Drawing Sheets

Latin name of the genus and species: *Dasiphora fruiticosa.*

Variety denomination: 'SMNPPS'.

BACKGROUND OF THE INVENTION

The present invention comprises a new and distinct variety of *Dasiphora* hereinafter referred to by the cultivar name. 'SMNPPS' This new *Dasiphora* was developed through a breeding program in Grand Haven, Mich. The objective of the breeding program was to develop new *Dasiphora* in new colors, and larger flowers. 'SMNPPS' is an internal advanced selection from an in-house breeding program. The open pollination date resulting in the new variety was in 2011. Selection of the new variety was made during 2014.

The first asexual propagation of 'SMNPPS' was carried out during 2014 by softwood cuttings at a poly greenhouse in Grand Haven, Mich. 'SMNPPS' has been found to retain its distinctive characteristics through successive asexual propagations. Multiple generations have been propagated, with the new variety characteristics reproduced true to type.

SUMMARY OF THE INVENTION

The following are the most outstanding and distinguishing characteristics of this new cultivar when grown under standard horticultural practices at Grand Haven, Mich.:

1. Large, single, pink flowers.
2. Round, compact plant.

COMPARISON WITH THE PARENT VARIETY

'SMNPPS' is similar to the seed parent *Dasiphora fruticose* 'Pink Dbl 2F2', in most horticultural characteristics. 'SMNPPS' however differs in the following:

1. New variety has single flowers, the seed parent has double flowers.

COMMERCIAL COMPARISON

'SMNPPS' is similar to the commercial variety *Dasiphora fruticosa* 'Kupinpa', U.S. Plant Pat. No. 22,732, in most horticultural characteristics. 'SMNPPS' however differs in the following:

1. Plants of the new variety produce single flowers, this comparator produces semi-double flowers.
2. Flowers of new variety have pink edges, fading to white towards center. Comparator's flowers have very pink petals from edges to center.

DESCRIPTION OF THE PHOTOGRAPHS

This new *Dasiphora* is illustrated by the accompanying photographs which show the plant's form, foliage and inflorescences. The colors shown are as true as can be reasonably obtained by conventional photographic procedures. Plants were grown in Grand Haven, Mich.

Figure 1:
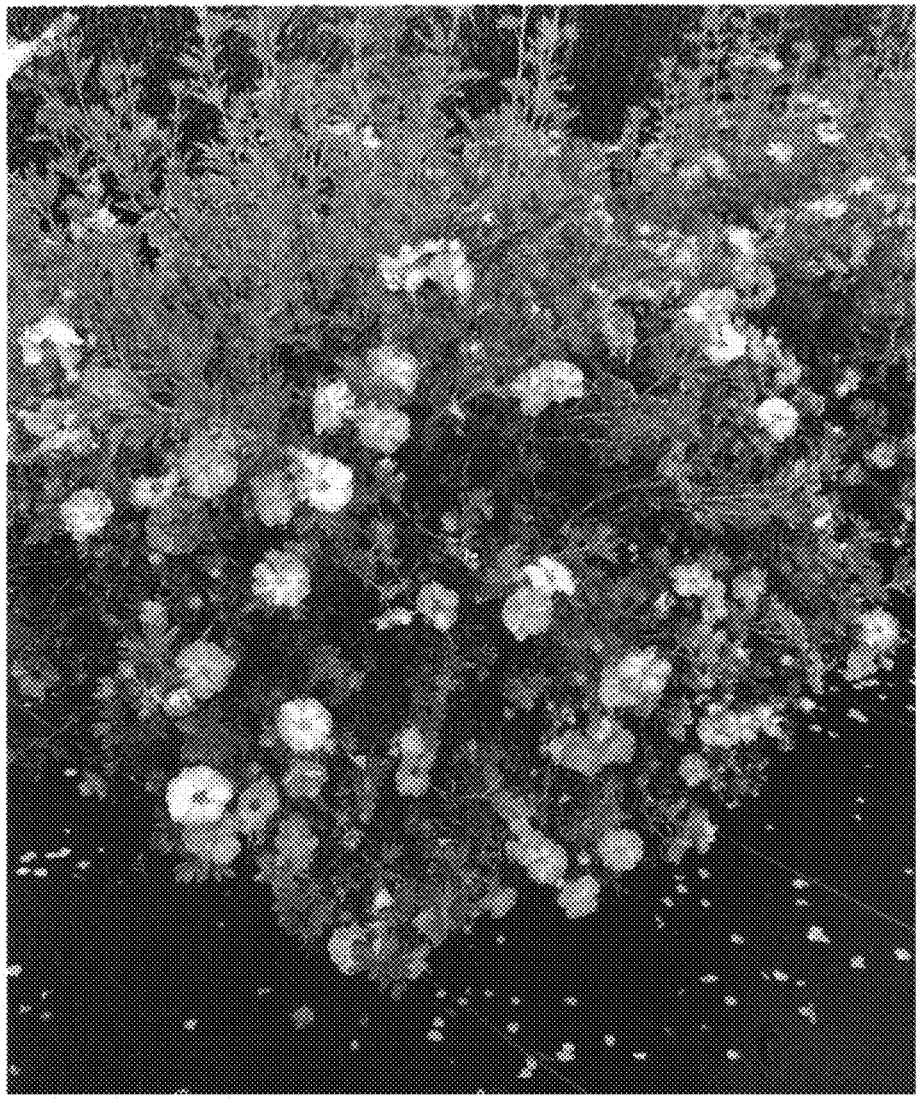

FIG. 1. Shows a flowering plant of 'SMNPPS' in a 2 gallon container at approximately 2 years old during Summer.

Figure 2:
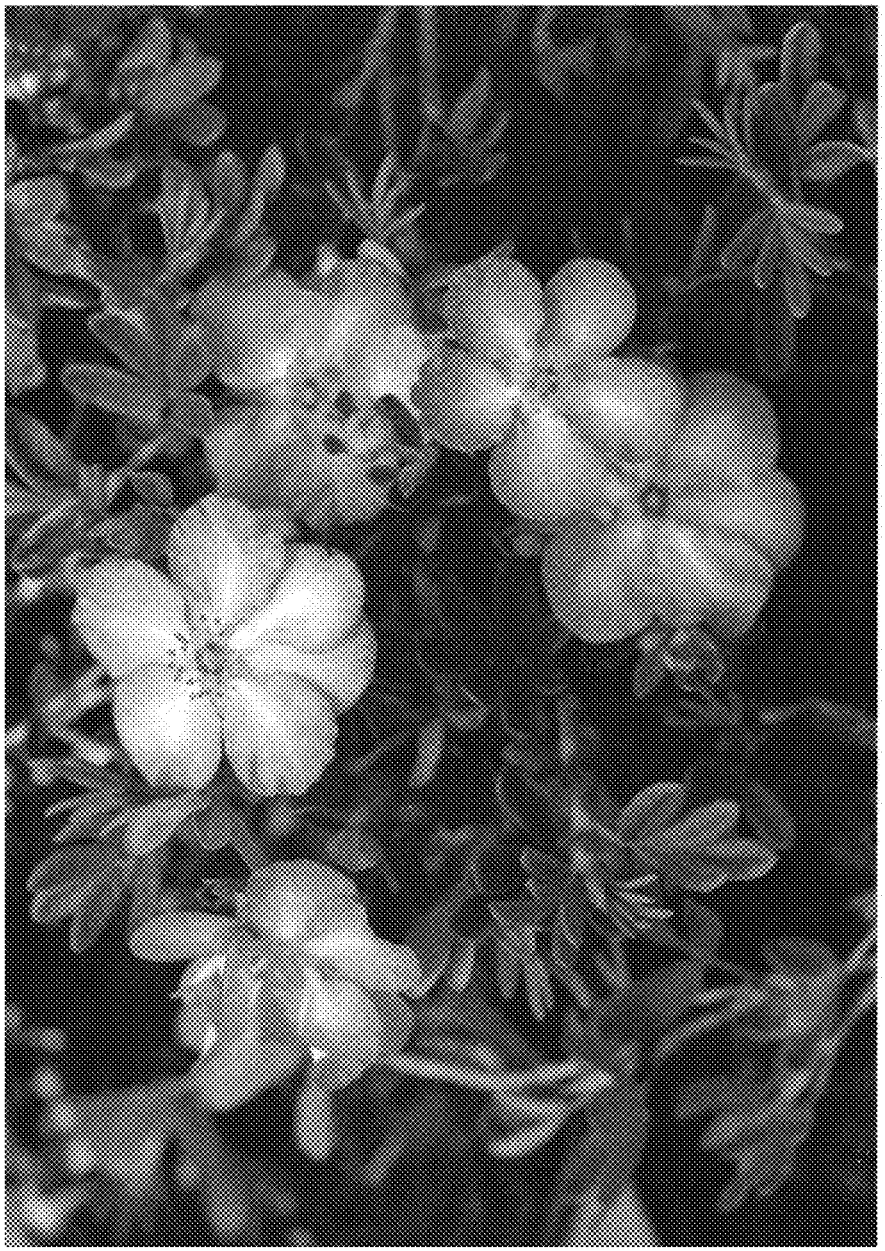

FIG. 2. Shows a close-up view of the flowers.

DESCRIPTION OF THE NEW CULTIVAR

In the following description, color references are made to The Royal Horticultural Society Colour Chart 2015 except where general terms of ordinary dictionary significance are used. The following observations and measurements describe 'SMNPPS' plants grown in a poly-greenhouse during Summer, in Grand Haven, Mich. USA. The growing temperature ranged from 18° C. to 27° C. during the day and from 5° C. to 10° C. during the night. General light conditions are natural sunlight. Measurements and numerical values represent averages of typical plant types.

DETAILED BOTANICAL DESCRIPTION

Botanical classification: *Dasiphora fruticosa* 'SMNPPS'.

Propagation:

Typical method: Softwood cuttings.

Time to initiate rooting: About 20 days at approximately 18° C. to 27° C.

Time to produce a rooted young plant: About 3 months at approximately 18° C. to 27° C.

Root description: Dense, free branching, thin, fibrous. Colored white and tan, not accurately measured with an R.H.S. chart.

Plant description:

- *Age of plant described.*—About 2 years in a 3 gallon container.
- *Growth habit.*—Upward and outward.
- *Height.*—26 cm.
- *Width.*—48 cm.
- *Growth rate.*—Moderate.
- *Typical commercial container sizes.*—#1, #2, #3, and #5.

Branches:

- *Branching habit.*—Freely branching.
- *Lateral branch quantity.*—Around 20.
- *Lateral branch length.*—36 cm.
- *Lateral branch diameter.*—3 mm.
- *Branch angle.*—0-90 degrees. Upright and outwards.
- *Branch strength.*—Flexible.
- *Branch color.*—New growth: Green 143D. Woody: Greyed-Brown 199A.
- *Internode length.*—1.5 cm.

Foliage:

Leaves:

- *Arrangement.*—Alternate. Palmately compound, typically 3 to 5 leaflets present.
- *Individual leaf.*—
- *Length.*—Average range 3.2 to 5.1 cm.
- *Width.*—Average range 2.8 to 3.9 cm.
- *Leaflet.*—
- *Length.*—1.5 cm.
- *Width.*—4 mm.
- *Shape.*—Oblanceolate to oblong.
- *Apex.*—Acute to obtuse.
- *Base.*—Cuneate.
- *Margin.*—Entire.
- *Texture upper surface.*—Soft, pubescent.
- *Texture lower surface.*—Soft, pubescent.
- *Color.*—Immature: Upper: Yellow-Green 144B. Lower: Green 143D. Mature: Upper: Green 138A. Lower: Green 138B.

Venation:

- *Color.*—Upper: Inconspicuous and indistinguishable from leaf blade. Lower: Inconspicuous and indistinguishable from leaf blade.

Petiole:

- *Length.*—4.5 mm.
- *Width.*—1 mm.
- *Texture.*—Pubescent.
- *Color.*—Upper side: Yellow-green 144B. Under side: Yellow-green 144B.

Inflorescence:

- *Description.*—Single, rotate flowers.
- *Flowering season.*—Spring.
- *Fragrance.*—None.

Flowers:

- *Flower diameter.*—3 cm.
- *Flower depth.*—3 mm.
- *Flower length.*—3 cm.
- *Flower angle.*—Upward and outward.
- *Persistent or self-cleaning.*—Self-Cleaning.

Flower bud:

- *Length.*—7 mm.
- *Diameter.*—7 mm.
- *Shape.*—Ovate.
- *Color.*—Yellow-white 158D.

Petals:

- *Number.*—5.
- *Arrangement.*—Whorl.
- *Length.*—13 mm.
- *Width.*—12 mm.
- *Shape.*—Obovate to orbicular.
- *Apex.*—Obtuse or rounded.
- *Margin.*—Entire, sinuate.
- *Texture.*—Upper side: Soft, smooth. Under side: Soft, smooth.
- *Color.*—Immature upper surface: Red-Purple 73A. Immature lower surface: Yellow-white 158D. Mature upper surface: Red-Purple 73C with some Red-Purple 73A around the edges. Base near and interior White N155A. Mature lower surface: White N155A. Fading upper surface: White N155C, thick margin near Red-Purple 73B.

Sepals:

- *Appearance.*—Widely triangular.
- *Arrangement.*—Single whorl.
- *Number of sepals.*—5.
- *Shape.*—Widely triangular.
- *Tip.*—Acute.
- *Base.*—Fused.
- *Margin.*—Entire.
- *Length.*—6 mm.
- *Width.*—3 mm.
- *Texture.*—Upper side: Pubescent. Under side: Pubescent.
- *Color.*—Mature, upper side: Yellow-green 151C. Mature, under side: Yellow-green 145C.

Peduncle:

- *Length.*—13 mm.
- *Width.*—1 mm.
- *Color.*—Yellow-Green Group 145B.
- *Texture.*—Pubescent.
- *Strength.*—Good.

Reproductive organs:

Gynoecium:

*Pistil number*.—About 30.

*Pistil length*.—0.5 mm.

*Stigma color*.—Yellow Group 7A.

*Style length*.—1 mm.

*Style color*.—Yellow Group 7A fades to Green-White 157A.

Androecium:

*Stamen number*.—Average 20.

*Filament length*.—1.5 mm

*Anther shape*.—Ovate.

*Anther length*.—1 mm.

*Anther color*.—Yellow-Orange Group 12A.

*Amount of pollen*.—Scarce.

*Pollen color*.—N/A.

OTHER CHARACTERISTICS

Fruit: Not observed to date.

Disease and insect resistance: No significant disease or pest resistance nor susceptibility have been observed.

Temperature range: Observed to tolerate temperatures between −33° C. and 36° C.

What is claimed is:

1. A new and distinct *Dasiphora* plant named 'SMNPPS' as illustrated and described herein.

* * * * *